United States Patent [19]

Mattoni

[11] Patent Number: 4,915,703
[45] Date of Patent: Apr. 10, 1990

[54] AMPOULE-SYRINGE

[75] Inventor: Guglielmo Mattoni, Rome, Italy

[73] Assignee: Sigma-Tau Industrie Farmaceutiche Riunite S.P.A., Rome, Italy

[21] Appl. No.: 253,244

[22] Filed: Oct. 4, 1988

[30] Foreign Application Priority Data

Oct. 9, 1987 [IT] Italy ............... 22200 A/87

[51] Int. Cl.$^4$ .............................. A61M 5/28
[52] U.S. Cl. .................... 604/200; 604/195; 604/240
[58] Field of Search ............... 604/192–198, 604/240–243, 87, 148, 200, 244, 403, 415–416

[56] References Cited

U.S. PATENT DOCUMENTS

| 1,115,561 | 11/1914 | Northey | 604/192 |
| 1,612,116 | 12/1926 | Heublein | 604/200 |
| 2,175,365 | 10/1939 | Saffir | 604/403 |
| 2,753,866 | 7/1956 | Koree | 604/200 X |
| 3,750,645 | 8/1973 | Bennett et al. | 604/403 X |

FOREIGN PATENT DOCUMENTS 428327  4/1926  Fed. Rep. of Germany ...... 604/414

Primary Examiner—Dalton L. Truluck
Attorney, Agent, or Firm—Notaro & Michalos

[57] ABSTRACT

The invention describes an ampoule-syringe comprising a single, substantially cylindrical body, divided by a central narrow neck portion in two compartments, constituting the ampoule and the syringe respectively, the narrow neck portion forming the housing for the needle. In order to detach the syringe from the ampoule it is sufficient to break the cylindrical shell at the narrow neck portion.

5 Claims, 1 Drawing Sheet

AMPOULE-SYRINGE

FIELD AND BACKGROUND OF THE INVENTION

The present invention relates to an ampoule-syringe consisting substantially of a cylindrical body, preferably made of glass, divided in two compartments by a narrow neck portion.

One compartment of the invention which is closed at one end, constitutes the ampoule filled with liquid, and the other compartment forms a syringe in which a piston is inserted, and which is sealed at the open end by a movable capsule, capable of keeping an inner sterile condition. The ampoule-syringe according to the invention is characterized by a special arrangement of its parts, which makes the use thereof extremely handy and easy if compared to other known devices.

Both for practical and sanitary reasons, it is often advisable to store injection products in the form of and ampoule-syringe, namely by directly inserting a product in the container that will form the syringe This both simplifies the various injection operations by avoiding handlings that could lead to mistakes in the medicine dosage, and maintains a hygiene condition.

In the thus made ampoule-syringes the piston rod that ejects the product cannot enter the syringe completely but protrudes from the syringe to a certain extent; this causes difficulties, also due to the need of securing the rod in this position during packaging and transport. Furthermore, other problems are caused by the necessity of providing suitable needle protecting means, to be removed before use.

SUMMARY OF THE INVENTION

The present invention provides an ampoule-syringe that is less bulky and cheaper than the known devices, consisting substantially of a single body divided to a central narrow neck, into two parts, one of them forming the real ampoule, and the other the syringe body.

The needle support, housed inside the ampoule, is fixedly secured to the narrow neck portion.

At the side where the piston is inserted, the syringe is closed by a capsule that provides hermetical sealing and sterile conditions.

In this way both the needle and the piston rod are sheltered by the same shell of which the ampoule-syringe consists, the latter thus resulting much handier to use and of less cumbersome size; further, many problems can be solved, connected with the packaging and-/or handling of products.

BRIEF DESCRIPTION OF THE DRAWINGS

The present invention will be now described in detail, with special reference to the attached drawings, in which.

DESCRIPTION OF THE PREFERRED EMBODIMENTS

Figure 1:
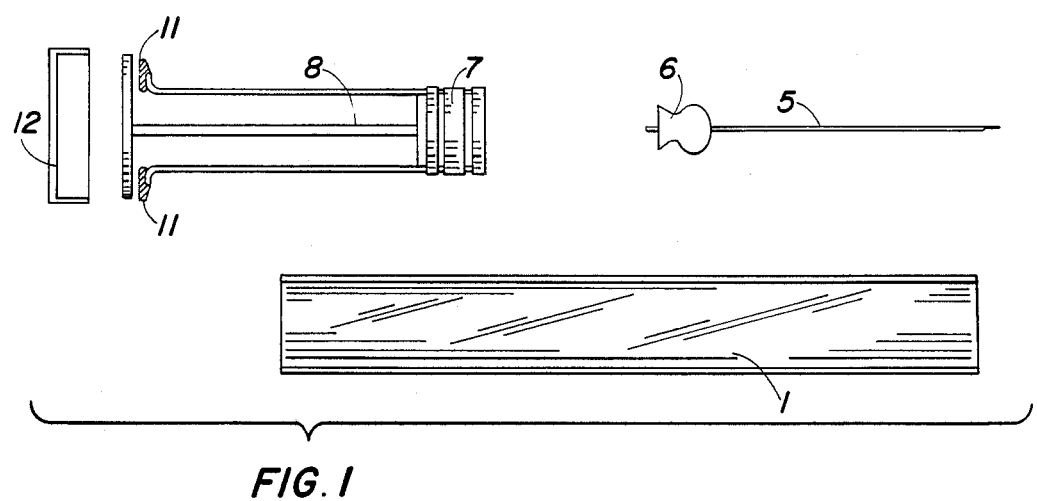
FIG. 1 is an exploded view of the ampoule-syringe according to the invention.

The ampoule-syringe according to the invention is made up of a cylindrical element 1 (see FIG. 1), made of glass or other suitable matter, opportunely shaped so as to have a first narrow neck portion 2 in the middle (see FIG. 2) and a second narrow neck portion 3 at one flared or V-shaped end 9.

At the side opposite narrow neck 3, cylinder 1 is shaped into an annular edge or rim 4.

The portion comprised between the narrow neck portions 2 and 3 is intended to form ampoule 14, and the portion comprised between the narrow neck portion 2 and rim 4 is intended to form syringe 15.

The ampoule-syringe is then completed by a needle 5 and a piston 7 provided with a rod 8. Needle 5 is secured to a support 6 that would either snap-fit—e.g. by resilient deformation of the matter which it consists of—or stand firmly blocked in position during the making of the narrow neck portion 2.

Figure 2:
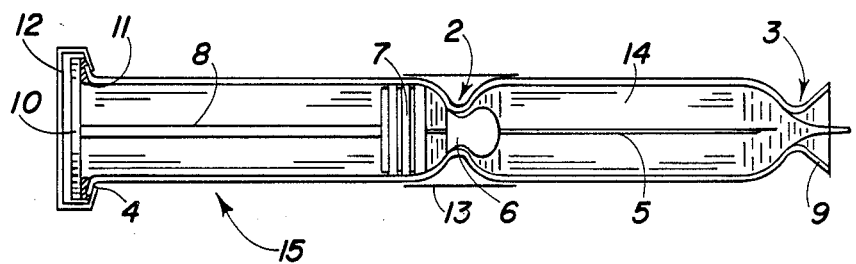
FIG. 2 in the ampoule-syringe according to the invention, assembled and ready to be filled with the pharmaceutical solution.

In the embodiment shown by FIGS. 1 and 2, support 6 of needle 5 consists of a substantially spherical body provided with a truncated cone-like projecting element, to the purpose of preventing said support from being pushed out of its seat by the pressure of the liquid being injected.

To the free end of rod 8 there is applied a substantially flat, round finger-rest or disc 10, which can be moved to first suck up the liquid form the ampoule-syringe, and then to exert a pressure on the piston during injection. The diameter of element 10 is slightly greater than the outer diameter of annular edge 4.

In between finger-rest 10 and rim 4 of the syringe an annular gasket 11 is inserted; the syringe is closed by a capsule or cover 12.

As evident from FIG. 2, the length of piston 7 with its rod 8, is less than the length of the syringe portion of the cylindrical element from the first narrow neck portion 2 to the rim 4, so that when the piston 7 is seated in its deepest position in the syringe, the disc 10 can seal the interior of the syringe by pressing against the gasket 11 and rim 4.

A sheath 13 provided with holes, made of flexible material, is arranged around the cylindrical body, in correspondence with the narrow neck portion 2 that separates the ampoule from the real syringe. As it will appear more clearly hereinafter, the perforated sheath 13 is for avoiding any possible fall of the ampoule after the user has broken up the ampoule-syringe making the suction of the ampoule content in the syringe easier and preventing the user from hurting himself with some fragments of glass.

The preparation and assembly of the components of the ampoule-syringe according to the invention are carried out by first shaping cylinder 1 so as to make therein narrow neck portions 2 and 3, and to form the V-shaped portion 9 and rim 4.

Then needle 5 is positioned by elastically inserting support 6 in the narrow neck portion 2. Alternatively, support 6 is clamped in position during the making of the narrow neck portion 2.

At this stage piston 7 is inserted in the syringe, that is hermetically sealed by capsule 12, after gasket 11 has been placed between finger-rest 10 and rim 4. After covering the central part with the perforated sheath 13, the ampoule-syringe is ready to be filled with the pharmaceutical solution. After filling, the V-shaped portion 9 is given the shape of the mouthpiece of a flute, closing thus ampoule 14.

The ampoule-syringe is now ready to use.

To this end, it is sufficient to remove capsule 12, break up the ampoule-syringe at the narrow neck portion 2 in order to detach the syringe from the ampoule and to suck up the liquid contained therein.

The advantages provided by the invention will appear from the above description. More specifically, it should be noted that all the ampoule-syringe components are perfectly protected during transport, as they are held inside the glass shell, while gasket 11 and capsule 12 provide a perfect sealing, and therefore a sterile ambient.

Of course the sizes, as well as the employed materials, can very in function of the various requirements of use.

What is claimed is:

1. An ampoule-syringe comprising:
   a cylindrical element (1) having one open end and an opposite closed end, said cylindrical element having an interior surface defining an interior space, said cylindrical element including a narrow neck portion (2) for dividing said interior space into a syringe space communicating with said open end and an ampoule space closed by said closed end;
   a needle support (6) in said narrow neck portion for separating said ampoule space from said syringe space;
   a needle (5) in said needle support, extending into said ampoule space;
   a syringe piston (7) mounted for sliding contact against the interior surface of said cylindrical element, in said syringe space;
   a piston rod having one end connected to said piston and an opposite end, said piston rod movable in said syringe space with movement of said piston,
   a finger-rest disc (10) fixed to the opposite end of said rod and engageable against said one open end of said cylindrical element for closing said one open end when said piston is adjacent said narrow neck portion, said piston rod and piston having an overall length which is less than the length of said cylindrical element from said narrow neck portion to said open end of said cylindrical element; and
   sealing means connected between said disc and said cylindrical element for sealing said disc to said one open end of said cylindrical element to seal said syringe space closed.

2. An ampoule-syringe according to claim 1 wherein said cylindrical element includes an outwardly extending rim (4) at said one open end thereof, said sealing means including a gasket (11) disposed between said disc and said rim for sealing said disc to said rim to seal said syringe space closed.

3. An ampoule-syringe according to claim 2 wherein said sealing means includes a capsule engaged over said disc and over a portion of said rim for holding said disc to said rim.

4. An ampoule-syringe according to claim 3 including a sleeve of deformable material engaged around said cylindrical element over said narrow neck portion for protecting a user when said cylindrical element is broken at said narrow neck portion to separate said ampoule space from said syringe space.

5. An ampoule-syringe according to claim 4 wherein said needle support is enlarged in both said syringe space and said ampoule space, on opposite sides of said narrow neck portion for retaining said needle support in said narrow neck portion even when said cylindrical element is broken at said narrow neck portion.

* * * * *